(12) United States Patent (10) Patent No.: US 9,285,306 B2
MacGregor et al. (45) Date of Patent: Mar. 15, 2016

(54) TEMPERATURE CALIBRATION METHODS AND APPARATUS FOR OPTICAL ABSORPTION GAS SENSORS, AND OPTICAL ABSORPTION GAS SENSORS THEREBY CALIBRATED

(75) Inventors: Calum John MacGregor, Ayr (GB); Desmond Robert Gibson, Argyll & Bute (GB)

(73) Assignee: GAS SENSING SOLUTIONS LTD., Cumbernauld (GB)

(*) Notice: Subject to any disclaimer, the term of this patent is extended or adjusted under 35 U.S.C. 154(b) by 116 days.

(21) Appl. No.: 13/882,902

(22) PCT Filed: Oct. 28, 2011

(86) PCT No.: PCT/GB2011/052110
§ 371 (c)(1),
(2), (4) Date: Jul. 9, 2013

(87) PCT Pub. No.: WO2012/059743
PCT Pub. Date: May 10, 2012

(65) Prior Publication Data
US 2013/0301052 A1 Nov. 14, 2013

(30) Foreign Application Priority Data

Nov. 1, 2010 (GB) .................................. 1018418.2

(51) Int. Cl.
*G01N 21/27* (2006.01)
*G01N 21/3504* (2014.01)
*G01N 33/00* (2006.01)

(52) U.S. Cl.
CPC .............. *G01N 21/27* (2013.01); *G01N 21/274* (2013.01); *G01N 21/3504* (2013.01);
(Continued)

(58) Field of Classification Search
CPC ....... G01N 1/22; G01N 1/40; G01N 21/3504; G01N 21/274; G01N 33/0006
USPC ........ 356/432–440, 243.1, 243.2; 702/24, 23, 702/31, 130; 73/23.24, 23, 24
See application file for complete search history.

(56) References Cited

U.S. PATENT DOCUMENTS

| 4,986,665 A | 1/1991 | Yamanishi et al. |
| 5,721,430 A | 2/1998 | Wong |

(Continued)

FOREIGN PATENT DOCUMENTS

| EP | 0 992 094 | 4/2000 |
| EP | 0992094 | 9/2002 |

(Continued)

OTHER PUBLICATIONS

International Search Report for PCT/GB2011/052110, mailed May 4, 2012.

(Continued)

*Primary Examiner* — Hoa Pham
(74) *Attorney, Agent, or Firm* — Nixon & Vanderhye P.C.

(57) ABSTRACT

An optical absorption gas sensor has an LED light source and a photodiode light detector, a temperature measuring device for measuring the LED temperature and a temperature measuring device for measuring the photodiode temperature. The sensor is calibrated by measuring the response of photodiode current at zero analyte gas concentration and at a reference analyte gas concentration. From these measurement, calibration data taking into account the effect of photodiode temperature on the sensitivity of the photodiode and, independently, the effect of changes in the spectrum of light output by the LED on the light detected by the photodiode with LED temperature can be obtained. Calibration data is written to memory in the gas sensor and in operation of the gas sensor, the output is compensated for both LED and photodiode temperature. The LED and photodiode can therefore be relatively far apart and operate at significantly different temperatures allowing greater freedom of optical pathway design.

17 Claims, 5 Drawing Sheets

(52) U.S. Cl.
CPC ... *G01N 33/0006* (2013.01); *G01N 2201/1211* (2013.01); *G01N 2201/12723* (2013.01); *G01N 2201/12753* (2013.01); *G01N 2201/12792* (2013.01)

(56) References Cited

U.S. PATENT DOCUMENTS

| | | | |
|---|---|---|---|
| 5,850,354 | A | 12/1998 | Bramley et al. |
| 8,265,881 | B1 * | 9/2012 | Lakhotia et al. ............. 702/24 |
| 8,649,012 | B2 * | 2/2014 | Beckmann et al. ........... 356/437 |
| 2006/0173637 | A1 * | 8/2006 | Martin .......................... 702/24 |
| 2007/0034792 | A1 | 2/2007 | Zhang et al. |

FOREIGN PATENT DOCUMENTS

| | | |
|---|---|---|
| EP | 0864180 | 7/2004 |
| JP | 62-217938 | 9/1987 |
| JP | 62-249033 | 10/1987 |
| JP | 2003-172695 | 6/2003 |
| JP | 2006-170845 | 6/2006 |
| JP | 2009-506329 | 2/2009 |
| KR | 10-0694635 | 3/2007 |
| KR | 10-2008-0076515 | 8/2008 |
| WO | WO 2005/015175 | 2/2005 |
| WO | 2007/091043 | 8/2007 |
| WO | WO 2008/072167 | 6/2008 |
| WO | 2009/019467 | 2/2009 |
| WO | WO 2009/019467 | 2/2009 |

OTHER PUBLICATIONS

Haigh et al., Applied Physics Letters vol. 90, 231116 (2007).

* cited by examiner

TEMPERATURE CALIBRATION METHODS AND APPARATUS FOR OPTICAL ABSORPTION GAS SENSORS, AND OPTICAL ABSORPTION GAS SENSORS THEREBY CALIBRATED

This application is the U.S. national phase of International Application No. PCT/GB2011/052110, filed 28 Oct. 2011, which designated the U.S. and claims priority to GB Application No. 1018418.2 filed 1 Nov. 2010, the entire contents of each of which are hereby incorporated by reference.

FIELD OF THE INVENTION

Background to the Invention

The invention relates to the field of optical absorption gas sensors which employ an LED (for example, an infra-red LED) as a source of light and a photodiode as a detector of light.

BACKGROUND TO THE INVENTION

Optical absorption gas sensors include both a source of light and a light detector. Light from the source is directed through a gas sample and detected by the light detector. The concentration of an analyte gas in the gas sample can be determined from the absorption of light by the analyte gas. Typically, either the source will emit light predominantly within a wavelength range corresponding to absorption lines of the intended analyte, or the detector will be sensitive to light predominantly within a wavelength range corresponding to absorption lines of the intended analyte, either due to the inherent properties of the light sensitive transducer which is employed or due to the presence of a wavelength filter which selects only light within a wavelength range including absorption wavelengths of the target analyte. Within this specification and the appended claims, light refers to electromagnetic radiation irrespective of wavelength and includes, for example, electromagnetic radiation in the infra-red region of the spectrum as this is a region within which many analyte gases have strong absorption lines.

The invention relates in particular to optical absorption gas sensors in which the source of light is an LED (for example, an infra-red LED) and the light sensitive transducer is a photodiode.

Light emitting diodes (LEDs) and photodiodes are inexpensive and relatively energy efficient devices and so they are commonly employed as sources and detectors of light in optical absorption gas sensors, particularly devices which are intended to be small and low cost. For many applications, an LED with a peak emission wavelength in the infra-red region of the spectrum, and a photodiode which is sensitive to infrared radiation are suitable.

LEDs and photodiodes are sensitive to a number of environmental factors, including temperature. Therefore in order to provide accurate measurements of analyte gas concentration, it is necessary to regulate the temperature of the LED and photodiode, or compensate for the temperature of the LED and photodiode, or to adopt another strategy. For example, in WO 2007/091043 (Gas Sensing Solutions Ltd.) the LED and photodiode are mounted substantially in thermal equilibrium. This latter strategy is advantageous in that a single temperature measurement may be made, for example, a measurement of the temperature of the LED, and the temperature of the other component can be inferred to be the same. This reduces the degrees of freedom of the system, simplifying temperature compensation in use. However, it provides constraints on the design of optical gas sensors, as the LED and photodiode must be mounted close to each other in order to be in thermal equilibrium.

In theory, it may be possible to independently calibrate the variation in optical properties of the LED with temperature, and the variation in optical properties of the photodiode with temperature, by entirely isolating the devices or independently controlling their temperatures. However, in practical, cost-effective manufacturing procedures, it is preferable to be able to carry out calibration using only measurements of photodiode output current from an assembled sensor, responsive to light from the LED within the assembled sensor, with the LED and photodiode at substantially the same temperature, without employing a procedure to independently change the temperature of the LED and a photodiode. Thus, in practice, it has been considered difficult to independently measure the change in optical properties of the LED and photodiode with temperature. If it was found that the photodiode output current dropped 10% due to a given change in temperature, this would imply that it would not be possible to determine to what extent that variation arose from changes in the optical properties of the LED, or optical properties of the photodiode, and so there would be no benefit to independently measuring the temperature of the LED and photodiode in use, as the effects of temperature on each component could not be separated.

The invention concerns the problem of manufacturing and calibrating optical absorption gas sensors having an LED and photodiode, to provide an output signal during operation of the resulting gas sensor which is accurate despite significant possible temperature differences between the LED and photodiode. Addressing this problem allows greater design freedom allowing more accurate, more energy efficient or cheaper sensors to be manufactured, and a further aspect of the invention concerns an improved configuration for an optical gas sensor waveguide.

SUMMARY OF THE INVENTION

According to a first aspect of the present invention there is provided a method of calibrating an optical absorption gas sensor for detecting an analyte gas, the sensor comprising a gas sample receiving chamber, a light emitting diode (LED) and a photodiode having an output signal (typically a current) sensitive to the amount of light received by the photodiode, the method comprising measuring the photodiode output signal at a first concentration and a different second concentration of the analyte gas within the gas sample receiving chamber, determining photodiode calibration data and determining LED calibration data.

Typically, the method further comprises making measurements of the output signal at a range of temperatures, at the first concentration of analyte gas within the gas sample receiving chamber. It may be that the photodiode calibration data is derived from the said measurement of the output signal at a range of temperatures.

Typically, the LED calibration data is derived from at least one measurement of the output signal at the first concentration and at least one measurement of the output signal at the second concentration of analyte gas in the gas sample receiving chamber.

The method may comprise making measurements of the output signal at a range of temperatures, at the second concentration of analyte gas within the gas sample receiving chamber. The LED calibration data may be derived from those measurements. It may be that the photodiode calibration data is substantially or entirely independent of the variation in the output signal at a range of temperatures measured at the second concentration of analyte gas within the gas sample receiving chamber. It may be that the photodiode calibration data is determined without taking into account measurements at the second concentration of analyte gas within the gas sample receiving chamber.

The invention also extends to a method of operating an optical absorption gas sensor calibrated by the method of the first aspect, comprising measuring the photodiode output signal, a parameter related to the temperature of the LED and a parameter related to the temperature of the photodiode, and determining a compensated signal representative of the concentration of the analyte gas in the gas sample receiving chamber taking into account each of the measured photodiode output signal, the measured parameter related to the temperature of the LED, the measured parameter related to the temperature of the photodiode, the LED calibration data and the photodiode calibration data.

The invention also extends to a method of measuring the concentration of an analyte gas comprising forming an optical absorption gas sensor, the sensor comprising a gas sample receiving chamber, a light emitting diode (LED) and a photodiode operable to output a photodiode output signal (typically a current) responsive to light incident on the photodiode from the LED after passing through the gas sample receiving chamber, an LED temperature measurement device to measure a parameter related to the temperature of the LED, a photodiode temperature measurement device to measure a parameter related to the temperature of the photodiode, and memory, the method comprising calibrating the sensor by a method according to the first aspect of the invention, storing the LED calibration data and the photodiode calibration data, or data derived therefrom, in the memory, and subsequently measuring the photodiode output signal, the parameter related to the temperature of the LED and the parameter related to the temperature of the photodiode, and calculating the concentration of the analyte gas taking into account the said data stored in the memory, the photodiode output signal, the measured parameter related to the temperature of the LED and the measured parameter related to the temperature of the photodiode. The photodiode output signal is typically a parameter related to the photodiode current, for example, a measurement of the photodiode current expressed in appropriate units.

By photodiode calibration data we refer to data usable to compensate a measurement of photodiode signal for photodiode temperature. By LED calibration data we refer to data usable to compensate a measurement of photodiode signal for LED temperature. The photodiode calibration data and LED calibration data may be integrated, for example, in the form of a lookup table of data relating photodiode signal to analyte gas concentration for each of a plurality of photodiode temperatures for each of a plurality of LED temperatures. The photodiode calibration data and LED calibration data may be independent. The parameter related to the temperature of the LED and/or the parameter related to the temperature of the photodiode may be the temperature of the LED and/or the temperature of the photodiode respectively, in any appropriate scale or units. However, it may not be necessary for the actual temperature to be calculated and the temperature of the LED and/or the temperature of the photodiode may be a signal output from a measurement device which is itself a function of the temperature of the LED or photodiode respectively, for example, a measurement of the forward voltage across the LED or photodiode respectively.

The sensitivity of a photodiode varies with temperature (amongst other factors) and the photodiode output current decreases as temperature increases. Typically, the photodiode is a broadband photodiode which is substantially insensitive to the wavelength of incident light over a range of wavelengths of at least 10% and preferably at least 25% of the strongest absorption line of the analyte gas which the optical sensor is adapted to measure. Thus, if the light from the LED is constant, the photodiode output current would depend on the temperature of the photodiode but the variation in the photodiode output current with the concentration of analyte gas as a proportion of the photodiode output current with no analyte gas should be substantially independent of temperature.

However, we have found that, although the light output of an LED also varies with temperature, within the context of an optical absorption gas sensor for measuring the concentration of an analyte gas, the predominant effect with temperature results from the change in wavelength of the light output by the LED rather than a change in the total amount of light emitted. Thus, although there will be some variation in the magnitude of the photodiode signal at zero analyte gas concentration with the temperature of the LED, this will not be the only effect. As the analyte gas will have absorption lines at defined wavelengths, a change in the spectral profile of the LED will change the proportion of the light from the LED which will be absorbed by a given concentration of analyte gas and therefore affect the sensitivity of the photodiode signal to analyte. A similar effect would also arise if the photodiode output current is sensitive to the wavelength of incident light around the wavelength of the strongest absorption line of the analyte gas which the sensor is configured to measure.

Thus, the variation in the photodiode output current with the concentration of analyte gas as a proportion of the photodiode output current with no analyte gas is not independent of the temperature of the LED.

As a result, the effect of temperature on the photodiode and the effect of temperature on the measured photodiode signal resulting from changes in the optical properties of the LED can be independently distinguished by carrying out measurements at first and second different concentrations of analyte gas.

The first concentration of analyte gas is typically negligible (e.g. zero).

For example, to a first level of approximation, the LED output can be assumed to be substantially independent of temperature enabling the photodiode calibration data to be determined at negligible (e.g. zero) analyte gas concentration. The LED calibration data can then be determined by measurements at the second (non-zero and non-negligible) concentration of analyte gas. Typically, measurements at the second (non-zero and non-negligible) concentration of analyte gas are carried out at a range of temperatures. The decrease in photodiode output current due to absorption by the analyte gas at the second (non-zero and non-negligible) concentration can be deduced, as this is substantially independent of temperature, and so the effect of the changes in optical properties of the LED with the temperature of the LED can be deduced. This can be carried out without, for example, requiring to selectively change the relative temperature of the LED and the photodiode during calibration or calibrating the LED and the photodiode entirely independently of the other, which is impractical for cost effective manufacturing.

Further accuracy can be obtained by still further measurements. Typically, the method comprises making measurements of the output signal at a plurality of concentrations of analyte gas within the gas sample receiving chamber, and at a plurality of temperatures (e.g. temperatures of the sensor as a whole or specifically the photodiode or specifically the LED). In some embodiments, the plurality of concentrations of analyte gas are at least three, or at least four, different concentrations of analyte gas. In some embodiments, the plurality of temperatures are at least three, or at least ten, different temperatures (which may, for example, be different temperatures of the LED, different temperatures of the photodiode and/or different ambient temperatures). For example, measurements of the output current may be made at a range of gas concentrations whilst the temperature is maintained at a first temperature and then further measurements of the output current may be made at a range of gas concentrations (typically the same range of gas concentrations) whilst the temperature is maintained at a second temperature. This may then be repeated at a third temperature and so forth. Measurements of the output current may also be made at a range of temperatures whilst the gas concentration is maintained at a first concentration (which may be zero) and further measurements of the output current may be made at a range of temperatures (typically the same range of temperatures) whilst the gas concentration is maintained at a second concentration. At each analyte gas concentration, the temperature may be swept across a temperature range. Typically a parameter related to the temperature of the LED and a parameter related to the temperate of the photodiode are measured at each of the concentrations of analyte gas and at each of the temperatures. A parameter related to ambient temperature may also be measured at each of the concentrations of analyte gas and at each of the temperatures.

Preferably, the sensor is configured so that the temperature of the LED and the temperature of the photodiode will remain within 5 degrees centigrade (and preferably within 2 degrees centigrade) during operation.

Preferably, the measured parameter related to the temperature of the LED is a parameter related to the temperature of the diode junction. The parameter related to the temperature of the LED may be, or may be derived from, a measurement of the forward voltage, $V_F$, of the LED, which is dependent of the temperature of the diode junction. Suitable circuits for determining temperature by measuring the forward voltage are disclosed in WO 2009/019467 (Gas Sensing Solutions Limited), the content of which is imported herein by virtue of this reference. Parameters related to temperature can be determined in other ways, using temperature sensitive components, for example the current through a thermistor in close proximity to the LED or photodiode respectively, might be employed.

During calibration, the LED calibration data and the photodiode calibration data may be stored in memory within the optical absorption gas sensor, for example, a PROM, EPROM or EEPROM. The LED calibration data and the photodiode calibration data are typically read from the memory (e.g. by a processor) during operation of the gas sensor. The LED calibration data and the photodiode calibration data may be stored as a lookup table including data from which the relationship between analyte gas concentration and photodiode output current can be deduced for each of a plurality of values of a parameter related to LED temperature and a plurality of values of a parameter related to photodiode temperature. Thus, the LED calibration data may take the form of a lookup table. The photodiode calibration data may take the form of a lookup table. The LED calibration data and the photodiode calibration data may take the form of a lookup table having at least two dimensions, one corresponding to a parameter related to LED temperature and one corresponding to a parameter related to photodiode temperature.

However, the photodiode calibration data may comprise one or more parameters (of an algorithm relating a property of the photodiode output signal to a parameter related to photodiode temperature). The LED calibration data may comprise one or more parameters (of an algorithm relating a property of the LED, or an effect of a property of the LED on the response of the photodiode output signal to analyte gas concentration, with a parameter related to temperature). The step of determining the compensated signal may comprise calculating at least one algorithm taking into account at least one said parameter, for example, at least one said parameter concerning photodiode calibration and/or at least one said parameter concerning LED calibration. The or each said parameter may comprise a scaling factor. For example, the photodiode calibration data may comprise a scaling factor by which the photodiode signal should be multiplied for a given parameter related to photodiode temperature. One or more said parameters may be coefficients of a polynomial (for example a $5^{th}$ order polynomial) or other numerical function (of the parameter related to temperature). For example, the LED calibration data may comprise one or more parameters of a polynomial relating an effect of the wavelength of LED light output on the sensitivity of the output signal to the parameter related to LED temperature).

The LED calibration data and the photodiode calibration data may take the form of a lookup table having at least two dimensions, one corresponding to the parameter related to LED temperature. The other dimension may correspond to the parameter related to photodiode temperature.

The compensated signal is preferably compensated for the temperature of the LED and the temperature of the photodiode. The compensated signal may be a signal proportional to the measured analyte gas concentration, or to the logarithm of the measure analyte gas concentration, or the compensated signal and may, for example, be proportional to the photodiode output signal (e.g. photodiode current), increased or decreased as appropriate to compensate for effects sensitive to the temperature of the LED and the temperature of the photodiode.

According to a second aspect of the present invention there is provided an optical absorption gas sensor comprising a gas sample receiving chamber, a light emitting diode (LED) and a photodiode operable to output a photodiode output signal (typically a current) responsive to light incident on the photodiode from the LED after passing through the gas sample receiving chamber, an LED temperature measurement device to measure a parameter related to the temperature of the LED, a photodiode temperature measurement device to measure a parameter related to the temperature of the photodiode, and a compensation module operable to output a compensated signal indicative of the concentration of an analyte gas within the gas sample receiving chamber taking into account the photodiode output signal, the measured parameter related to the temperature of the LED and the measured parameter related to the temperature of the photodiode. For example, the compensation module may comprise an electronic circuit configured to output a compensated signal indicative of the concentration of an analyte gas within the gas sample receiving chamber taking into account the photodiode output signal, the measured parameter related to the temperature of the LED and the measured parameter related to the temperature of the photodiode, or a processor executing program code (stored on a computer readable storage medium) which causes the processor to determine a compensated signal indicative of the concentration of an analyte gas within the gas sample receiving chamber taking into account the photodiode output signal, the measured parameter related to the temperature of the LED and the measured parameter related to the temperature of the photodiode.

The compensation module is preferably operable to take into account stored calibration data concerning the variation in photodiode output signal with a parameter related to LED temperature and (independently) with a parameter related to photodiode temperature. The stored calibration data may be, or be derived from, photodiode calibration data and LED calibration data obtained by the method of the first aspect of the invention. Where the stored calibration data is or comprises a parameter of an algorithm, the compensation module is typically operable to (e.g. configured to or programmed to) calculate at least one algorithm taking into account the or each stored parameter. The stored parameter may be a scaling factor and a said algorithm may be a multiplication. Preferably, the algorithm is non-linear. Some or all of the stored parameters may be parameters of a polynomial, or other function. The compensation module may take into account an anticipated photodiode output signal at zero analyte gas concentration for a measured parameter related to photodiode temperature and a measured parameter related to LED temperature. Thus, the compensation module may be operable to compensate for differences in the amplitude of the photodiode output signal for a given analyte gas concentration at different temperatures of the LED and at different temperatures of the photodiode.

The compensation module may compensate for differences in the ratio of photodiode output signal (e.g. current) for a given analyte gas concentration to photodiode current for zero analyte gas concentration with LED temperature (indicated by the measured parameter related to LED temperature). Thus, it may be operable to output a signal indicative of a first analyte gas concentration and a signal indicative of a second analyte gas concentration in response to measurement of a first photodiode output signal and a second photodiode output signal, where the ratio of the first photodiode output signal to the second photodiode output signal varies with LED temperature (for at least a range of first and second analyte gas concentrations and LED temperature).

In operation, the step of determining the compensated signal may comprise the step of multiplying the photodiode output signal (e.g. photodiode current) by a compensation factor dependent on the measured parameter related to photodiode temperature. The step of determining the compensated signal may then comprise the further step of determining the difference between the product of the photodiode output signal and the compensation factor and a reference value. The step of determining the compensated signal may then comprise correcting the said difference taking into account the LED calibration data. This step may comprise making a non-linear correction for the parameter related to LED temperature.

One skilled in the art will appreciate that the parameter related to temperature of the LED and the parameter related to the temperature of the photodiode could be measured by measuring a parameter related to the temperature of one of the LED and the photodiode and by measuring a parameter related to the temperature difference between the LED and the photodiode.

The LED, the photodiode and the gas sample receiving chamber are configured so that light from the light emitting diode passes through the gas sample receiving chamber, is optionally reflected one or more times, onto the photodiode. Thus, the concentration of a target gaseous analyte within the gas sample receiving chamber can be determined from the attenuation of electromagnetic radiation within a wavelength range measured by the photodiode.

Typically, the sensitivity of the photodiode signal to received light is not substantially sensitive to the wavelength of the received light, at least in a wavelength band within which the peak output light intensity of the LED varies in an operating temperature range of the optical absorption gas sensor.

The LED and the photodiode may be formed in semiconductors with the same substrate and/or epilayer composition and structure, typically with different doping. The LED and the photodiode may be formed from indium aluminium antimonide material ($(In_{1-x})Al_xSb$), grown on a gallium arsenide (GaAs) substrate.

The light emitting diode and photodiode may each be formed from a narrow band gap III-V material indium aluminium antimonide material ($(In_{1-x})Al_xSb$), grown on a gallium arsenide (GaAs) substrate, the doping of which is chosen to tune the band gap to cause the light emitting diode to emit light of a narrow wavelength range corresponding to a wavelength at which the intended analyte (e.g. gaseous carbon dioxide) absorbs strongly. The formation of suitable light emitting diodes and photodiodes are disclosed in EP 0 864 180, EP 0 992 094, and in Haigh, M. K. et al., Applied Physics Letters, vol. 90, 231116 (2007), the contents of each of these documents being incorporated herein by virtue of this reference.

Optional features described above in relation to the first or second aspect of the invention are optional feature of both the first and second aspects of the invention.

In a third aspect, the invention extends to an optical absorption gas sensor comprising a gas sample receiving chamber, a light emitting diode (LED) and a photodiode operable to output a photodiode output signal (typically a current) responsive to light incident on the photodiode from the LED after passing through the gas sample receiving chamber, an LED temperature measurement device to measure a parameter related to the temperature of the LED, a photodiode temperature measurement device to measure a parameter related to the temperature of the photodiode, and a compensation module operable to output a compensated signal taking into account stored calibration data, wherein the stored calibration data was obtained by the method of the first aspect of the invention. The stored calibration data is typically stored in a memory, such as a PROM, EPROM or EEPROM.

The invention extends in a fourth aspect to an optical absorption gas sensor for detecting an analyte gas, the sensor comprising a gas sample receiving chamber, a light source (e.g. a light emitting diode) and a photosensor (e.g. a photodiode) operable to generate an output signal (e.g. a current) sensitive to the amount of light received by the photosensor, wherein the inward wall of the gas sample receiving chamber is reflective and defines a first compound parabolic collector having the light source therein and a second compound parabolic collector having the photosensor therein, opposite the first compound parabolic collector.

Typically, the first and second compound parabolic collectors intersect. Thus, substantially all, or all, of the inward walls of the gas sample receiving chamber may be defined by the two opposite intersecting compound parabolic collectors. Typically, the inward wall of the gas sample receiving chamber is rotationally symmetric extending around and axis extending from the light source to the photosensor. Thus, the gas sample receiving chamber is typically elongate and straight.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
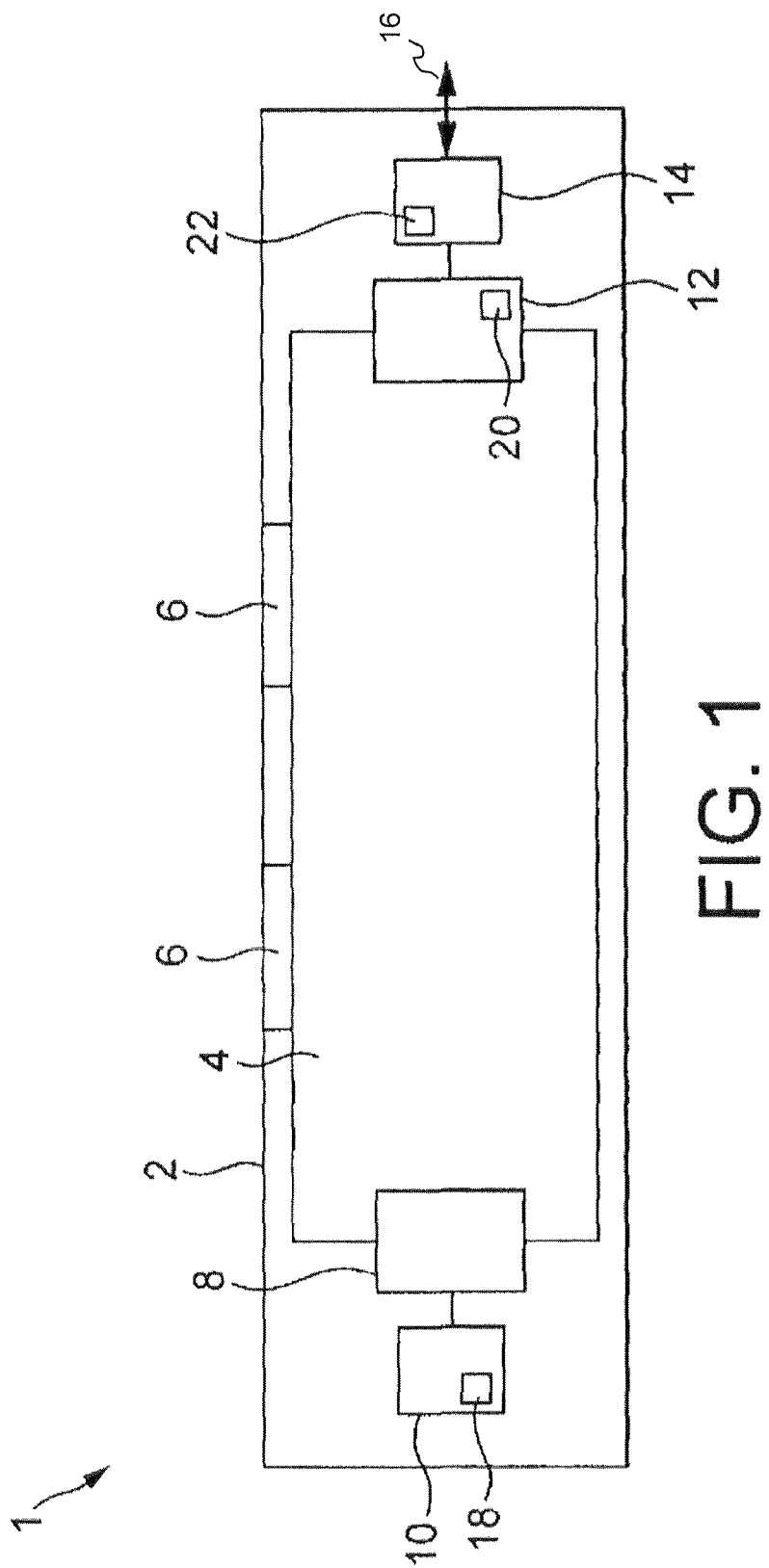
FIG. 1 is a schematic diagram of an optical absorption gas sensor according to the present invention.

With reference to FIG. 1, an optical absorption gas sensor 1 has a body 2 defining a gas sample chamber 4, into which a gas sample can pass by diffusion through one or more apertures 6. A light emitting diode 8 functions as a light source, and is driven by an LED driving circuit 10. A photodiode 12 functions as a photosensor, and has an output current dependent on the light which falls on the photodiode junction. The current from the photodiode is amplified and processed by a control and compensation circuit 14 including a microcontroller, which provides a compensated signal through an output 16 which is related to the concentration of analyte gas in the gas sample chamber.

Figure 5:
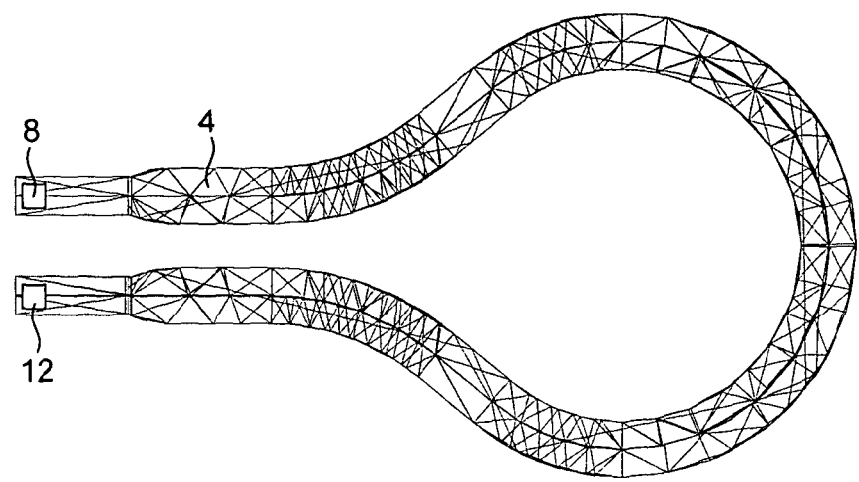
FIG. 5 is a cross-section through the optical path of a first optical absorption gas sensor.
Figure 6:
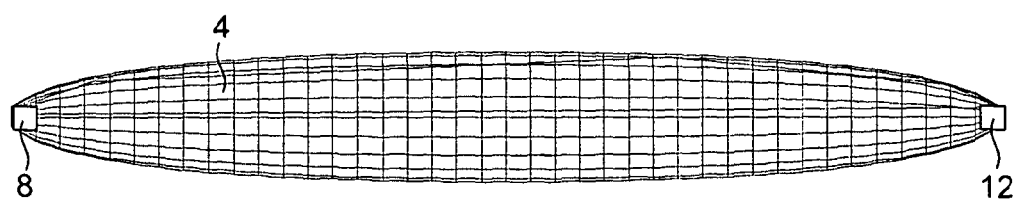
FIG. 6 is a cross-section through the optical path of a second optical absorption gas sensor.

The gas sample chamber may have any of a large number of configurations known to those skilled in the art, and typically includes a reflective inner surface, so that light from the LED may be reflected one or more times between the LED and a photodiode. An example configuration is illustrated in FIG. 5 or 6 and discussed further below. The LED and photodiode may be located adjacent to each other, or further apart. The optical arrangement is selected so that the attenuation of light within a wavelength characteristic of a target analyte affects the current from the photodiode. Thus, the LED may have a defined range of output wavelengths (albeit sensitive to temperature), the photodiode may be sensitive to a defined range of output wavelengths and/or a wavelength band pass filter may be provided.

The LED driving circuit includes a temperature sensing circuit 18. The temperature sensing circuit determines the temperature of the LED photodiode by measuring the forward voltage, $V_f$, across the LED and a photodiode respectively. Suitable circuits for determining temperature by measuring the forward voltage are disclosed in WO 2009/019467 (Gas Sensing Solutions Limited). A thermistor 20 is mounted to the photodiode to enable measurement of the temperature of the photodiode. Other components which are sensitive to temperature could be employed, for example a resistance wire (e.g. platinum wire) or a thermocouple. The temperature of the photodiode could also be determined from its forward voltage, $V_F$.

The control and compensation circuit includes a memory 22 storing two lookup tables. The first stores a compensation factor A, for each of a plurality of photodiode temperatures. The second stores one or more compensation values B, for each of a plurality of LED temperatures. A and B were calculated and stored during a calibration step when the sensor was manufactured, which is discussed further below In use, the control and compensation circuit determines the gas concentration from the measured photodiode current, measured LED temperature and measured photodiode temperature, by the following procedure. The value of compensation factor A associated with the measured photodiode temperature is obtained, either by directly employing a value stored in the first lookup table or by interpolating between values stored for a temperature above and below the measured photodiode temperature. The photodiode current, S, is then multiplied by A. This gives a signal which is independent of photodiode temperature but which is affected by the presence of the target analyte gas. This temperature compensated signal level, S×A, is then compared with the signal level expected when no target gas is present (typically the magnitude of the values of A were calculated taking into account this predetermined product of photodiode current and A when no target gas is present) and the difference, D, is calculated. D is indicative of absorption by analyte.

The measured LED temperature is then used to look up one or more compensation values B. Again, if there is not a value or values of B for the precise measured LED temperature, B is obtained by interpolation between values of B for higher and lower temperatures. In some embodiments, B is a scaling factor, and the sensor outputs D×B as a compensated output signal, C. In other embodiments, the values of B are coefficients of a non-linear function. In one embodiment, there are several values of B, which are coefficients of a $5^{th}$ order polynomial which is calculated thereby giving a compensated output signal which is a multiple of D that is a non-linear function of temperature. Where a $5^{th}$ order polynomial (or other algorithm) is employed, the parameters of the equation (coefficients in the case of a polynomial) can be individually obtained by interpolation, or, potentially more accurately, the algorithm can be calculated at each of two different temperatures, comprising at least one above and at least one below the measured LED and the resulting values used in interpolation. In a further embodiment, the values of B are values of a lookup table of measured gas concentration versus absorption D for a respective LED temperature. In an example embodiment, 27 lookup tables are provided, one for each of 27 different measured LED temperatures, each of which relates D to gas concentration. If the measured LED temperature is not the same as one of the temperatures for which a lookup table is provided, the gas concentration (functioning as the compensated signal) is determined by interpolation between tables for higher and lower temperature.

Thus, the output signal is derived from the measured photodiode current, but compensated for both photodiode temperature and LED temperature. As the compensation for LED temperature can be non-linear, the compensation for LED temperature can take into account effects arising from changes in the spectrum of light output by the LED, rather than simply a change in the amount of light output by the LED.

The data stored in the lookup table is written to the memory after a calibration procedure when the sensor is first manufactured. The sensor is assembled, with the LED and photodiode mounted within the sensor, either in or adjacent the gas sample receiving chamber, so that at least the optical pathway, and typically the entire gas sensor, has already been assembled before calibration begins.

A first calibration gas including only a negligible concentration of the target analyte which the sensor is designed to detect, is introduced to the gas sensor. It diffuses into the gas sample receiving chamber. The gas sensor is powered up, the light emitting diode emits light, and measurements are taken of the photodiode output current. The temperature is varied across a selected range of temperatures, and the response of the photodiode output current to temperature is thereby measured. The sensor is exposed to a second calibration gas which includes a defined concentration of the target analyte. Once the second calibration gas has equilibrated within the gas sample receiving chamber, the temperature is again varied across a selected range of temperatures, and the response of the photodiode output current to temperature, in the presence of the second calibration gas, is thereby measured. This procedure is repeated, for example, employing four or five calibration gases having different concentrations of analyte gas.

The response of the photodiode output current to temperature when no analyte gas is present is a function of the change in the amount of current produced per unit light incident on the photodiode with temperature. Thus, the values of A can be determined from the response of the photodiode output current with temperature at substantially zero analyte gas concentration.

The values of B are determined from the response of the photodiode output current with LED temperature obtained at each of the several calibration gas concentrations. In some embodiments, the photodiode signal S is multiplied by the value of A calculated for the current photodiode temperature, and this is compared with the signal level expected when no target gas is present and the difference, D, calculated as during subsequent operation of the device. The value or values of B which would lead to C being correctly calculated are then determined and stored in a lookup table for the applicable LED temperature and analyte gas concentration. In some embodiments, where the values of B are coefficient of a polynomial, the value of B which cause the polynomial to best fit the correction output signals, C, are calculated and stored.

Thus, the resulting sensor can compensate for both the effect of photodiode temperature on the sensitivity of the photodiode and the non-linear effect of LED temperature on the wavelength profile of light emitted by the LED.

In some embodiments, the actual temperature of the LED and the photodiode is never calculated as such. Instead, other measured properties related to the temperature of the LED and/or photodiode are used as proxies. For example, the forward voltage across the LED is a property related to the temperature of the LED and in some embodiments, the forward voltage is measured and values B are stored for each of a number of values of the forward voltage. Thus, the forward voltage across the LED is used as a proxy for LED temperature during calibration and operation. Similarly, the current from the thermistor can be used as a proxy for photodiode temperature during calibration and operation as it is related to the temperature of the photodiode. In this case, values of A are stored for each of a plurality of values of the current through the thermistor and are looked up during operation based on the measured current through the thermistor.

Figure 2:
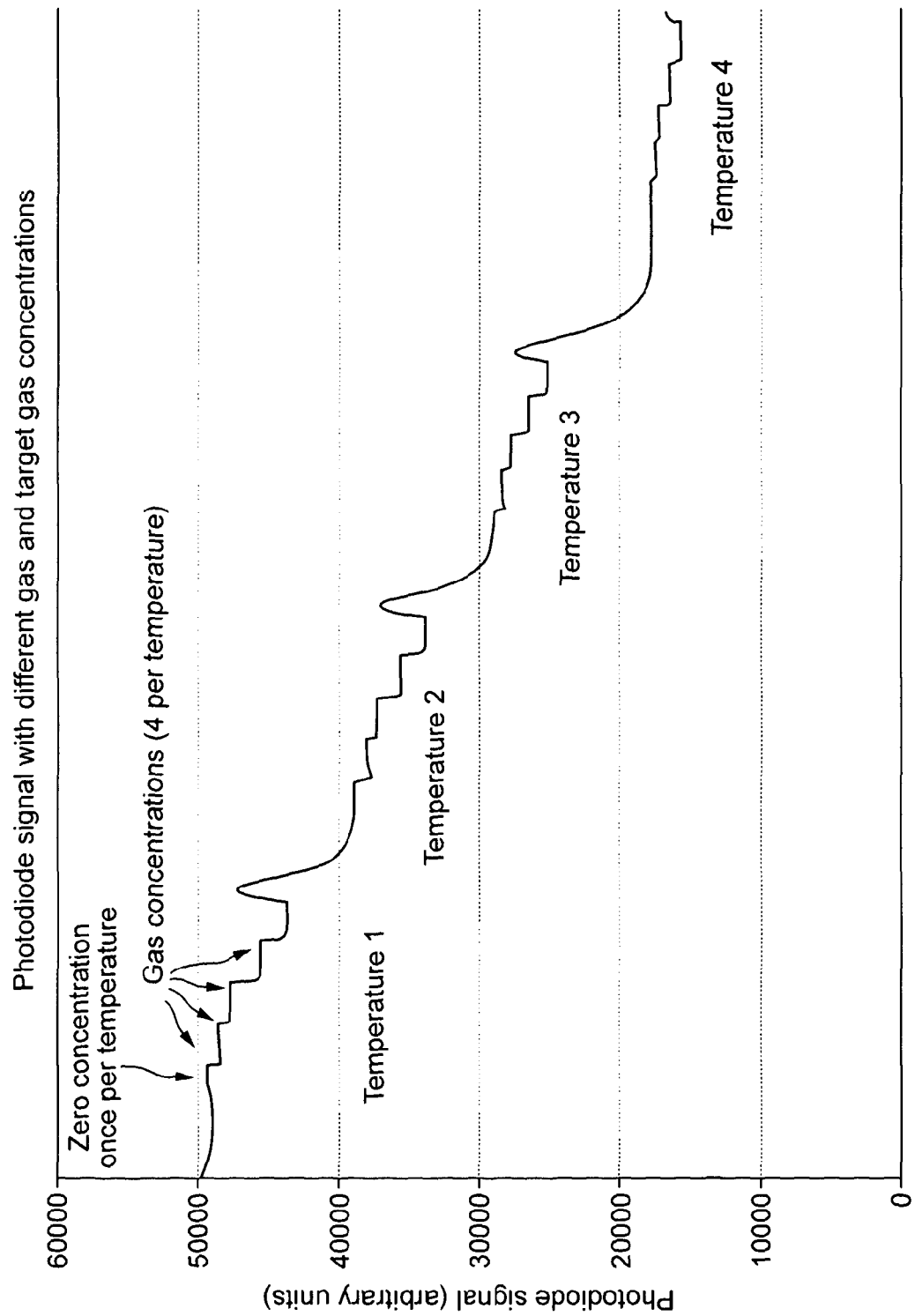
FIG. 2 is a graph of photodiode signal at different gas concentrations, at each of four different temperatures.
Figure 3:
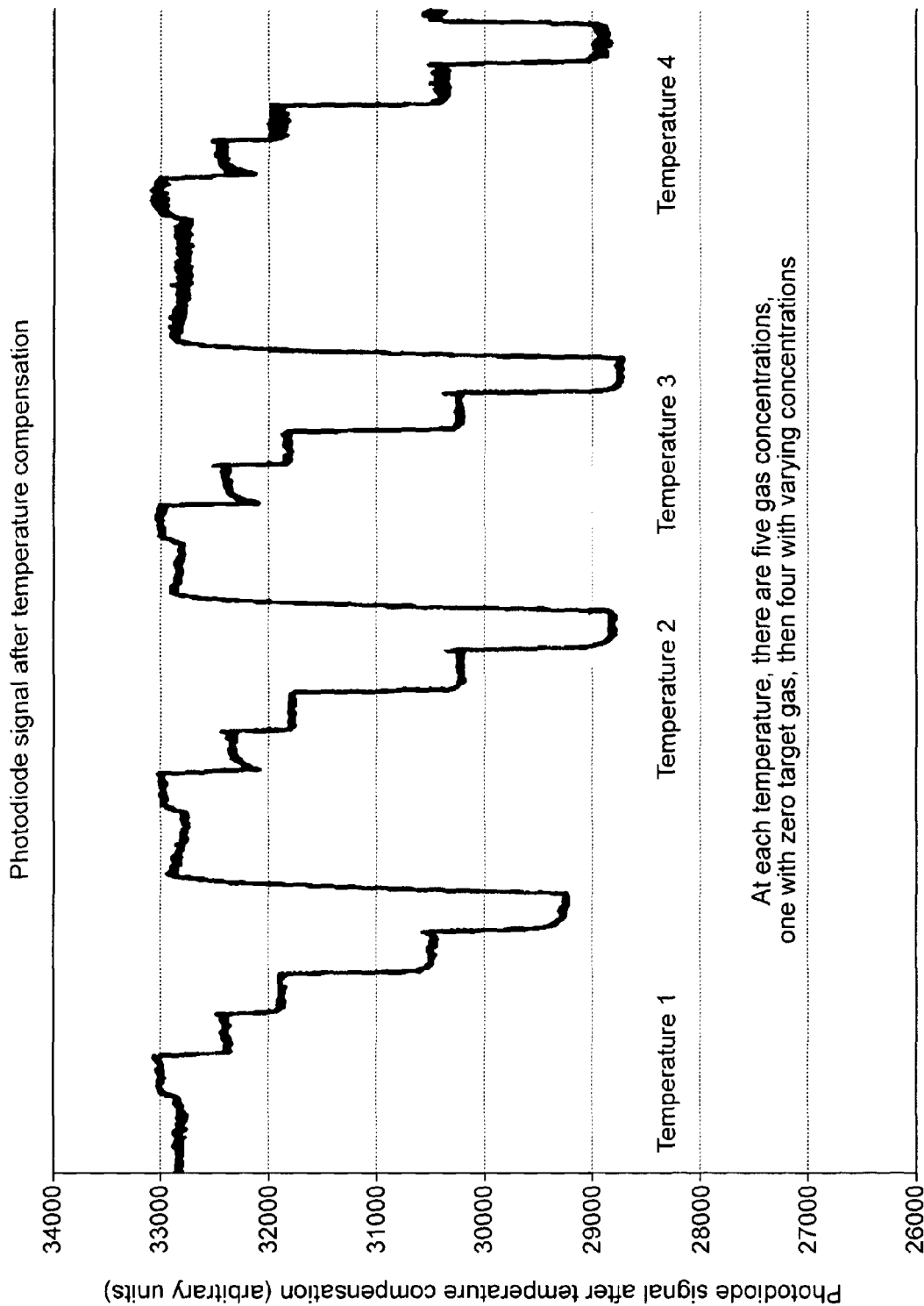
FIG. 3 is a graph of photodiode signal compensated for photodiode temperature.
Figure 4:
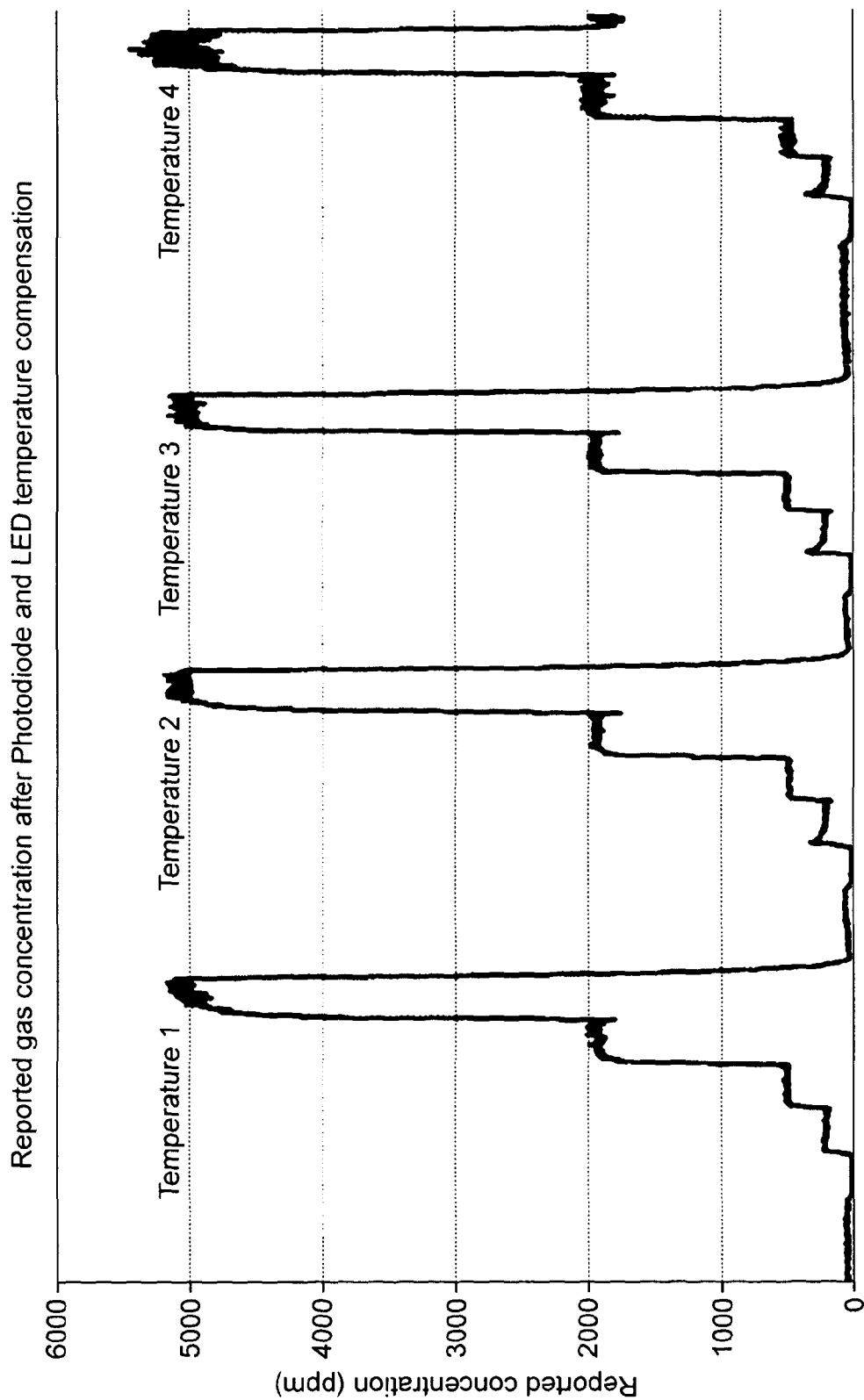
FIG. 4 is a graph of compensated output signal (reported gas concentration) after compensation for both photodiode temperature and LED temperature.

FIGS. 2 through 4 illustrate experimental data from an example embodiment. FIG. 2 shows the photodiode output signal on an arbitrary linear scale (Y-axis) versus time (X-axis) at a zero concentration of an analyte gas ($CO_2$ in this example) then four different non-zero gas concentrations, repeated at the same gas concentrations, in the same order, at each of four different temperatures. The same data, after compensation for photodiode temperature (S×A) is illustrated in FIG. 3, and the reported gas concentration signal, C, after further compensation for LED temperature, is illustrated in FIG. 4.

By providing a sensor having an output which is compensated for LED temperature and, independently, photodiode temperature, the LED and photodiode may be further apart than would otherwise be possible. For example, a first gas sensor was simulated having an optical pathway shown in cross-section in FIG. 5. The proportion of light emitted by the LED received at the photodiode was 59.6% assuming the waveguide is coated with a high-quality gold coating, and 23.7% assuming the waveguide is coated with a low-quality gold coating. However, when a gas sensor was simulated having an optical pathway as shown in cross-section in FIG. 6, the proportion of light emitted by the LED and received at the photodiode was 82.8% (high-quality gold coating) or 62.1% (low-quality gold coating). Thus, by removing the constraint that the LED and photodiode must be close together, to remain at substantially the same temperature, there is greater freedom for the optical design of the sensor, allowing a higher efficiency (maximum proportion of emitted light received at the photodiode), or lower-quality and therefore lower cost reflective coatings to be employed for the same sensitivity.

The waveguide of FIG. 6 is formed from two opposed compound parabolic collectors, which face each other. In this arrangement, the majority of light is reflected only two to four times, once or twice on each parabolic collector. As demonstrated by the proportions quoted above of light reaching the LED reaching the photodiode, this provides an efficient configuration for a waveguide in an optical gas sensor.

The optical gas sensor may be adapted to detect an analyte such as carbon dioxide, carbon monoxide, methane, water vapour (to measure humidity) etc. by selecting the LED and photodiode to generate and detect light specifically at one or more wavelengths where the analyte gases absorb strongly.

Further variations and modifications may be made within the scope of the invention herein disclosed.

The invention claimed is:

1. A method of calibrating an optical absorption gas sensor for detecting an analyte gas, the sensor comprising a gas sample receiving chamber, a light emitting diode (LED) and a photodiode having an output signal sensitive to the amount of light received by the photodiode, the method comprising measuring the photodiode output signal at a first concentration and a different second concentration of the analyte gas within the gas sample receiving chamber, and thereby determining photodiode calibration data and determining LED calibration data based on the measured photodiode output signal at the first concentration and the different second concentration of the analyte gas within the gas sample receiving chamber.

2. A method according to claim 1, wherein the method further comprises making measurements of the output signal at a range of temperatures, at the first concentration of analyte gas within the gas sample receiving chamber.

3. A method according to claim 1, wherein the LED calibration data is derived from at least one measurement of the output signal at the first concentration of analyte gas within the gas sample receiving chamber and at least one measurement of the output signal at the second concentration of analyte gas within the gas sample receiving chamber.

4. A method according to claim 1, wherein the method comprises making measurements of the output signal at a range of temperatures, at the second concentration of analyte gas within the gas sample receiving chamber.

5. A method according to claim 4, wherein the photodiode calibration data is substantially or entirely independent of the variation in the output signal at a range of temperatures measured at the second concentration of analyte gas within the gas sample receiving chamber.

6. A method according to claim 1, wherein the first concentration of analyte gas is negligible.

7. A method according to claim 1, wherein the method comprises making measurements of the output signal at least three concentrations of analyte gas within the gas sample receiving chamber, and at at least three different temperatures.

8. A method according to claim 1, wherein a parameter related to the temperature of the LED is determined by measuring forward voltage, $V_F$, of the LED.

9. A method according to claim 1, wherein the LED calibration data and the photodiode calibration data are stored in memory within the optical absorption gas sensor.

10. A method according to claim 1, wherein the LED calibration data comprises parameters of a non-linear algorithm.

11. A method of operating an optical absorption gas sensor calibrated by the method of claim 1, comprising measuring the photodiode output signal, a parameter related to the temperature of the LED and a parameter related to the temperature of the photodiode and determining a compensated signal representative of the concentration of the analyte gas in the gas sample receiving chamber taking into account each of the measured photodiode output signal, the measured parameter related to the temperature of the LED, the measured parameter related to the temperature of the photodiode, the LED calibration data and the photodiode calibration data.

12. A method of operating an optical absorption gas sensor according to claim 11, wherein the compensated signal is compensated for the temperature of the LED and the temperature of the photodiode.

13. A method of operating an optical absorption gas sensor according to claim 11, wherein the step of determining the compensated signal comprises the step of multiplying the photodiode output signal by a compensation factor dependent on the measured parameter related to the temperature of the photodiode.

14. A method of operating an optical absorption gas sensor according to claim 13, wherein the step of determining the compensated signal further comprises the step of determining the difference between the product of the photodiode output signal and the compensation factor and a reference value, and then correcting the said difference taking into account the LED calibration data.

15. A method of operating an optical absorption gas sensor according to claim 11, comprising the step of making a non-linear correction for LED temperature.

16. A method of measuring the concentration of an analyte gas comprising forming an optical absorption gas sensor, the sensor comprising a gas sample receiving chamber, a light emitting diode (LED) and a photodiode operable to output a photodiode output signal responsive to light incident on the photodiode from the LED after passing through the gas sample receiving chamber, an LED temperature measurement device to measure a parameter related to the temperature of the LED, a photodiode temperature measurement device to measure a parameter related to the temperature of the photodiode, and memory, the method comprising calibrating the sensor by a method according to claim 1, storing the LED calibration data and the photodiode calibration data, or data derived therefrom, in the memory, and subsequently measuring the photodiode output signal, the parameter related to the temperature of the LED and the parameter related to the temperature of the photodiode, and calculating the concentration of the analyte gas taking into account the said data stored in the memory, the photodiode output signal, the measured parameter related to the temperature of the LED and the measured parameter related to the temperature of the photodiode.

17. An optical absorption gas sensor comprising a gas sample receiving chamber, a light emitting diode (LED) and a photodiode operable to output a photodiode output signal responsive to light incident on the photodiode from the LED after passing through the gas sample receiving chamber, an LED temperature measurement device to measure a parameter related to the temperature of the LED, a photodiode temperature measurement device to measure a parameter related to the temperature of the photodiode, and a compensation module operable to output a compensated signal taking into account stored calibration data, wherein the stored calibration data was obtained by the method of claim 1.

* * * * *